US007657307B2

(12) United States Patent
Van Dam et al.

(10) Patent No.: US 7,657,307 B2
(45) Date of Patent: Feb. 2, 2010

(54) METHOD OF AND APPARATUS FOR CLASSIFYING ARRHYTHMIAS USING SCATTER PLOT ANALYSIS

(75) Inventors: Peter M. Van Dam, Doesburg (NL); Joanneke G. Groen, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 664 days.

(21) Appl. No.: 11/263,184

(22) Filed: Oct. 31, 2005

(65) Prior Publication Data

US 2007/0100248 A1 May 3, 2007

(51) Int. Cl.
*A61B 5/04* (2006.01)
(52) U.S. Cl. .................. 600/515; 600/508; 600/509; 600/512; 600/523; 128/920; 128/922; 128/923
(58) Field of Classification Search ......... 600/508–509, 600/512, 515, 523; 128/920, 922, 923
See application file for complete search history.

(56) References Cited

U.S. PATENT DOCUMENTS

| 4,732,157 | A | * | 3/1988 | Kaplan et al. ............... 600/509 |
| 5,404,880 | A | | 4/1995 | Throne |
| 5,622,178 | A | | 4/1997 | Gilham |
| 6,230,059 | B1 | | 5/2001 | Duffin |
| 6,490,479 | B2 | | 12/2002 | Bock et al. |
| 7,269,454 | B2 | * | 9/2007 | Sherman ..................... 600/515 |
| 2002/0065473 | A1 | | 5/2002 | Wang et al. |
| 2004/0092836 | A1 | | 5/2004 | Ritscher et al. |

FOREIGN PATENT DOCUMENTS

WO WO9802209 1/1998

OTHER PUBLICATIONS

"Do Existing Measures of Poincare Plot Geometry Reflect Nonlinear Features of Heart Rate Variability?" Brennan et al., IEEE Trans Biomed Eng. Nov. 2001;48(11):1342-7. Related Articles, Links Department of Electrical and Electronic Engineering, The University of Melbourne, Parkville, Victoria, Australia.

* cited by examiner

*Primary Examiner*—Carl H Layno
*Assistant Examiner*—Deborah Malamud
(74) *Attorney, Agent, or Firm*—Stephen W. Bauer

(57) ABSTRACT

A method of classifying arrhythmias using scatter plot analysis to define a measure of variability of a cardiac rhythm parameter such as for example, without limitation, R-R interval, A-A interval, and the slope of a portion of a cardiac signal, is disclosed. The variability measurement is derived from a scatter plot of a cardiac rhythm parameter, employing a region counting technique that quantifies the variability of the cardiac rhythm parameter while minimizing the computational complexity. The method may be employed by an implantable medical device or system, such as an implantable pacemaker or cardioverter defibrillator, or by an external device or system, such as a programmer or computer. The variability measurement may be correlated with other device or system information to differentiate between atrial flutter and atrial fibrillation, for example. The variability information may also be used by the device or system to select an appropriate therapy for a patient.

17 Claims, 8 Drawing Sheets

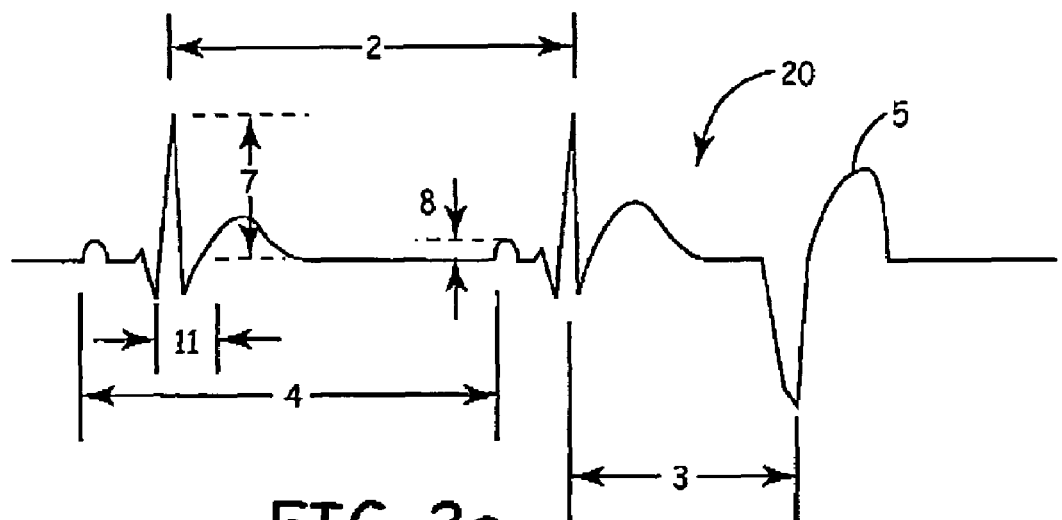
FIG. 2a
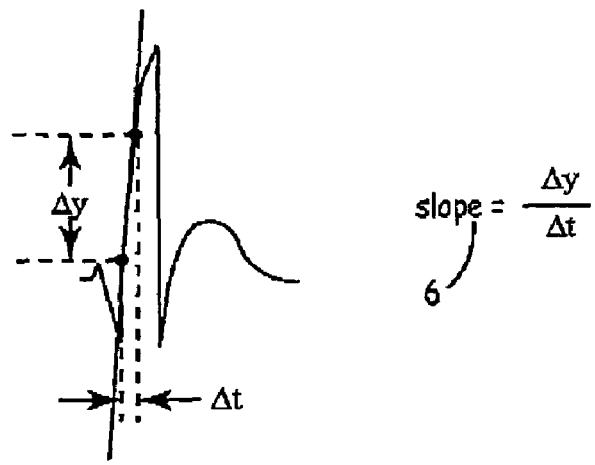
FIG. 2b
| R-R interval (msec) | Δ R-R interval |
|---|---|
| 31: 700 | — |
| 32: 750 | 50 |
| 33: 720 | 30 |
| 34: 725 | 5 |
| 35: 705 | 20 |
| 36: 730 | 25 |
| 37: 715 | 15 |
FIG. 2c

METHOD OF AND APPARATUS FOR CLASSIFYING ARRHYTHMIAS USING SCATTER PLOT ANALYSIS

FIELD

Most of the embodiments of the disclosure relate generally to a method of classifying arrhythmias in implantable medical devices, and more particularly, to a method and apparatus for discriminating atrial fibrillation from atrial flutter using a measure of variability of a cardiac rhythm parameter.

BACKGROUND

A variety of techniques have been developed for collecting and interpreting data concerning the electrical activity of the heart. Some techniques use external medical devices (EMDs) in the clinical setting, and others use implantable medical devices (IMDs).

Implantable cardiac monitors, such as the MEDTRONIC® Reveal™ insertable loop recorder, have also been developed and clinically implanted that employ the capability of recording cardiac electrogram (EGM) data for subsequent interrogation and uplink telemetry transmission to an external programmer for analysis by a medical care provider. The recorded data may be retrieved using an external programmer operated by a medical care provider. The programmer may include the ability to display the retrieved EGM data and/or perform processing and analysis functions on the retrieved EGM data. Stored segments of data can be transmitted via telemetry transmission to an external device for further analysis when a telemetry session is initiated. Aspects of the Reveal™ insertable loop recorder are disclosed in commonly assigned PCT publication WO98/02209 and in U.S. Pat. No. 6,230,059, the disclosures of which are hereby incorporated by reference in their entirety.

Scatter-plots, sometimes referred to as Lorentz or Poincaréplots, have been used to plot EGM and electrocardiograph (ECG) data. For example, U.S. Pat. No. 5,622,178 issued to Gilham describes a system and method for dynamically displaying cardiac interval data using scatter-plots. Consecutive R-R intervals form a coordinate pair (e.g., the "x" and "y" coordinates) of a point that is plotted on the scatter-plot. Subsequent points are plotted by "sliding" one heartbeat to the next group of successive heartbeats (i.e., the second, third, and fourth heartbeats) and plotting the next pair of R-R intervals. FIG. 1 illustrates an example of this technique in plotting R-R interval data on a scatter plot. Such scatter-plots may provide a visual indication of the variability of the parameter plotted.

Published Patent Application No. 2002/0065473 compares a number of consecutive R-R interval differences with a predetermined value to measure ventricular rate stability as part of a method to detect atrial fibrillation. A counter is incremented every time the measured R-R interval difference exceeds a threshold value, and classifies a rhythm as AF when a threshold total number is reached. Published Patent Application No. 2004/0092836 discloses an AF detection algorithm that uses a Cluster Signature Metric (CSM) that is based on the two-dimensional distribution of "first order lag" of R-R interval differences. Each of the above references is incorporated by reference herein in its entirety.

In atrial fibrillation (AF), the atria depolarize at an elevated rate that is highly irregular. The irregular nature of the ventricular response during AF is characterized by fluctuations in the intervals between ventricular contractions. In atrial flutter (AFL), the atria beat at an elevated rate that is highly regular, and a certain portion of the atrial depolarizations may be conducted to the ventricles in a predictable pattern. There are many instances where it is desirable to be able to diagnose intermittent spontaneous cardiac arrhythmias, particularly AF and AFL, in ambulatory patients. Atrial rate may serve as a criterion for distinguishing between AFL and AF. For example, AFL (types I and II) may typically occur at rates that can range from about 220 to about 450 bpm, and AF typically occurs at rates greater than about 300 bpm. However, since a significant range of overlap exists between AF and AFL, and since the range of overlap may be even greater in patients taking anti-arrhythmic drugs and/or in elderly patients, a method of distinguishing them that does not rely solely on rate is needed.

A method and system for performing scatter-plot analysis to classify cardiac rhythms is desired which minimizes computational resource requirements and allows for real-time processing of cardiac signals. A method of using such real-time data to affect therapy selection decisions (e.g., by an IMD) is also desirable.

SUMMARY OF THE INVENTION

In certain embodiments of the invention, a method of classifying arrhythmias includes the steps of acquiring a cardiac signal; deriving a recurring cardiac rhythm parameter from the cardiac signal and storing the information derived as a series of values; plotting a point on a scatter plot for each pair of successive stored values, the abscissa of each plotted point being equal to a first value of a pair of successive stored values, and the ordinate of each plotted point being equal to a second value of the pair of successive stored values, the scatter plot being divided into a plurality of regions; deriving a measure of variability by counting the number of regions in which one or more points are plotted; and comparing the measure of variability to a threshold value to classify the rhythm. In certain other embodiments of the invention, a system for classifying arrhythmias includes a sensor for acquiring a cardiac signal; a processor for deriving a recurring cardiac rhythm parameter from the cardiac signal and storing it as a series of values; a database for plotting a point on a scatter plot for each pair of successive stored values, the abscissa of the point being the first of a pair of successive stored values, and the ordinate of the point being the second of the pair of successive stored values, and wherein the scatter plot is divided into a plurality of regions; a processor for deriving a measure of variability by counting the number of regions in which one or more points are plotted; and a comparator for comparing the measure of variability to a threshold to classify the rhythm.

In another embodiment of the invention, an implantable medical device for classifying arrhythmias includes sensing means for acquiring a cardiac signal; processing means for deriving a recurring cardiac rhythm parameter from the cardiac signal and storing it as a series of values; plotting means for plotting a point on a scatter plot for each pair of successive stored values, the abscissa of the point being the first of a pair of successive stored values, and the ordinate of the point being the second of the pair of successive stored values, and wherein the scatter plot is divided into a plurality of regions; a processor for deriving a measure of variability by counting the number of regions in which one or more points are plotted; and a comparator for comparing the measure of variability to a threshold to classify the rhythm.

DESCRIPTION OF THE DRAWINGS

FIGS. 2(a)-(c) illustrate a cardiac signal and various cardiac rhythm parameters derived therefrom.

DETAILED DESCRIPTION

Figure 1:
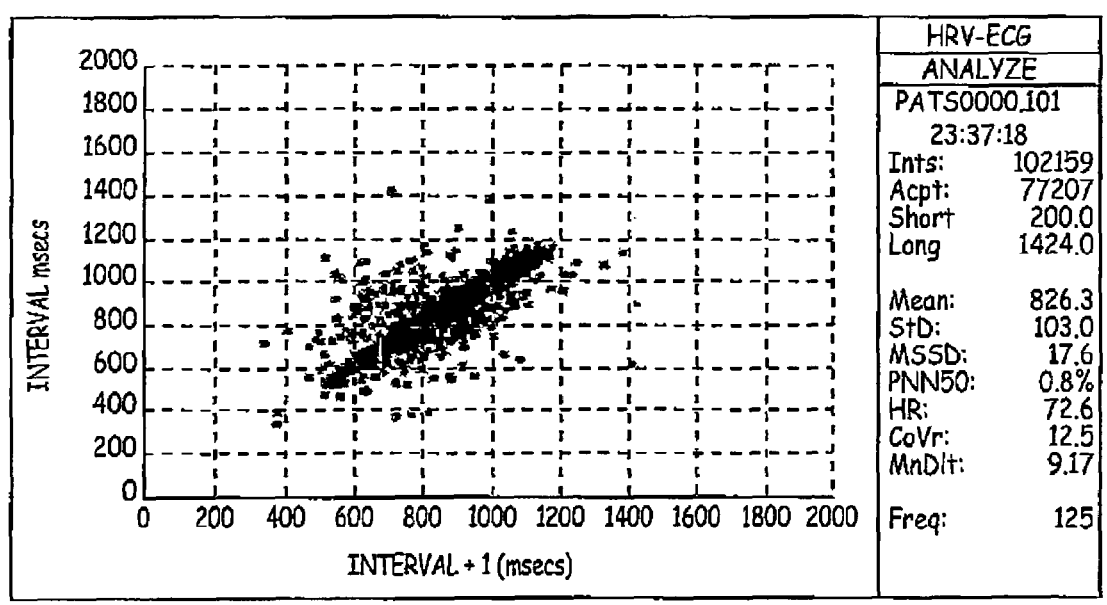
FIG. 1 is an example of a scatter plot of R-R interval data.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

FIGS. 2(a)-(c) show examples of various cardiac rhythm parameters derived from a cardiac signal 20. Cardiac signal 20 may be acquired from an ECG recording or from an EGM signal, for example. Acquiring a cardiac signal from an ECG recording may, for example, include recording electrical signals from sensors (surface leads) placed on the skin of a patient as is known in the art. Acquiring a cardiac signal from an EGM signal typically includes recording electrical signals from one or more sensors (leads) implanted in a patient either within or in relative close proximity to a chamber of a heart. EGM signals may be far-field, showing timing and morphological information associated with the entire heart, similar to that shown by an ECG, or they may be near-field, showing timing and amplitude information of a single area or chamber of the heart.

One cardiac rhythm parameter often used to analyze heart rhythms is the R-R interval 2, as shown in FIG. 2(a). Also shown in FIG. 2(a) is an R-R interval 3 between a "normal" R-wave and a PVC 5. The R-R interval is an example of a recurring cardiac rhythm parameter, since it can be derived or measured on a repeating basis. Other recurring cardiac rhythm parameters that may be useful for analysis include, but are not limited to, the following examples: P-P interval 4, R-wave amplitude 7, P-wave amplitude 8, Q-T interval 11, and R-wave slope 6, as shown in FIGS. 2(a) and (b). FIG. 2(c) shows one example of a recurring cardiac rhythm parameter, Δ R-R interval 9, that may be derived from another recurring cardiac rhythm parameter (in this case, from the R-R intervals). Another recurring cardiac rhythm parameter that may be derived from R-R intervals is ventricular rate. Ventricular rate, for example, may be calculated as a function of the R-R interval 2, using the equation:

$$\text{Rate}_{vent} \text{ (bpm)} = 60{,}000/(R\text{-}R \text{ Interval, msec}).$$

One of ordinary skill in the art would appreciate that other recurring cardiac rhythm parameters may be similarly derived from a cardiac signal 20 and used in accordance with embodiments of the invention, and would therefore fall within the scope of the claimed invention.

Figure 3A:
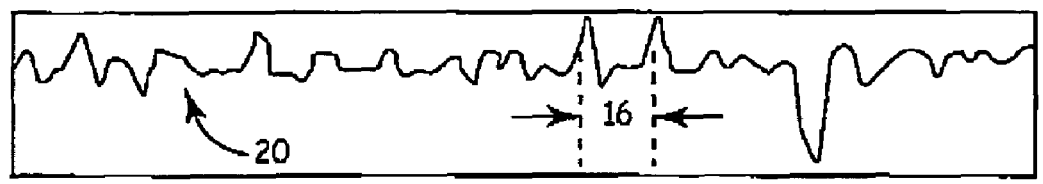
FIGS. 3(a) and (b) illustrate a cardiac signal and a scatter plot derived therefrom in accordance with an embodiment of the invention.
Figure 3B:
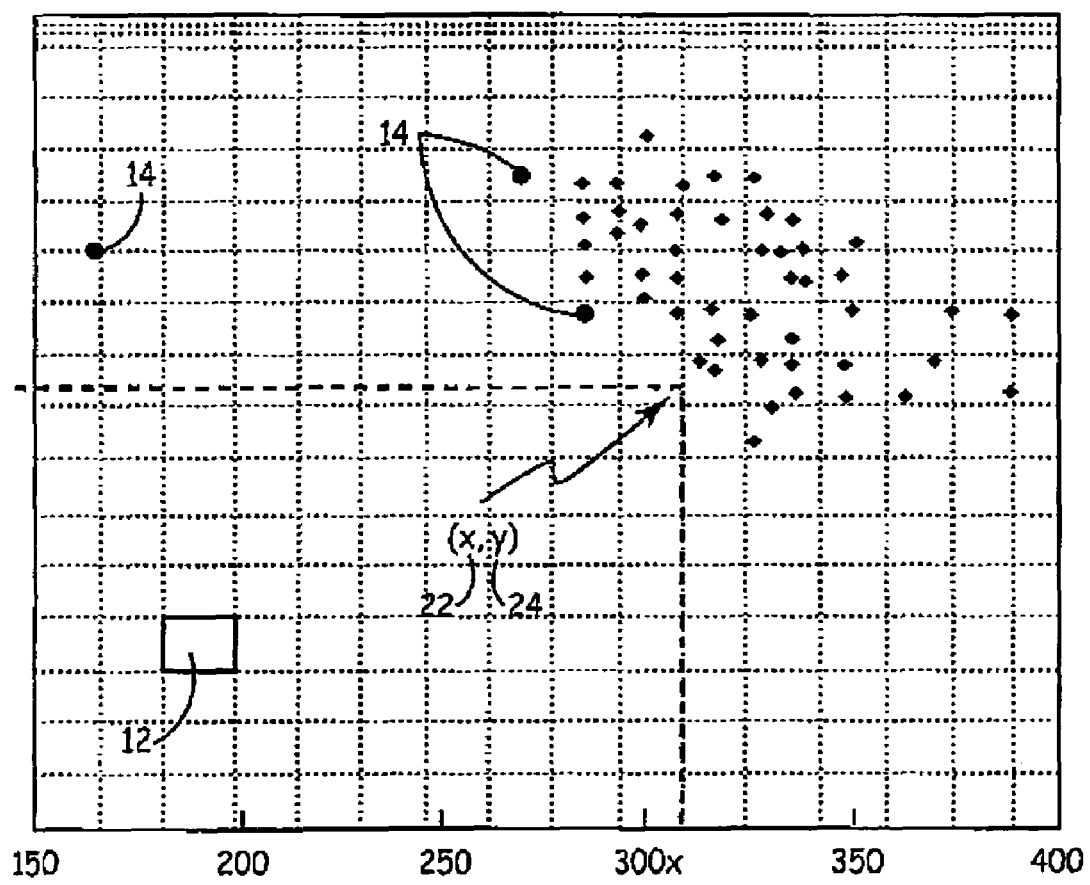

FIG. 3(b) shows an example of a scatter plot 10 derived from the cardiac signal 20 shown in FIG. 3(a). A series of cardiac rhythm parameters 16, such as R-R intervals, may be derived from the cardiac signal 20 as described above. The scatter plot 10 is formed by plotting points 14 thereon. Each point 14 is characterized by an x-coordinate (abscissa 22), and a y-coordinate (ordinate 24), as shown. Note that FIG. 3(a) may only show a portion of the cardiac signal 20 corresponding to scatter plot 10 in FIG. 3(b), since FIG. 3(a) is a time plot of cardiac signal 20, and since FIG. 3(b) is a scatter plot 10 which condenses a large number of points 14 (N=100) corresponding to a large number of R-R intervals into a relatively small plot area.

To illustrate the plotting of points 14 onto a scatter plot 10, the series of R-R intervals shown in FIG. 2(c) may be plotted based upon pairs of R-R intervals 31-37 as follows: A first point may have an abscissa of 700 msec and an ordinate of 750 msec corresponding to the first pair of R-R intervals 31, 32. A second point may have an abscissa of 750 msec and an ordinate of 720 msec corresponding to the second pair of R-R intervals 32, 33. Third and subsequent points are plotted following this same pattern. It should be noted that the choice of abscissa as the first value of each pair of values, and of ordinate as the second value of each pair of values, is somewhat arbitrary; the order could be reversed and would provide an equivalent result without departing from the scope of the invention. See FIG. 1.

Figure 4A:
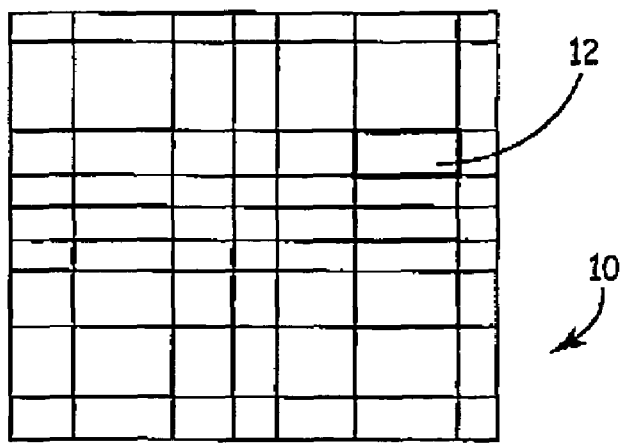
FIGS. 4(a)-(c) are examples of alternate embodiments of a scatter plot in accordance with embodiments of the invention.
Figure 4B:
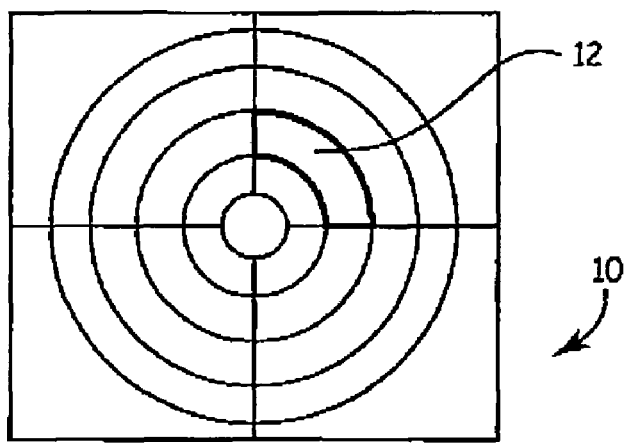
Figure 4C:
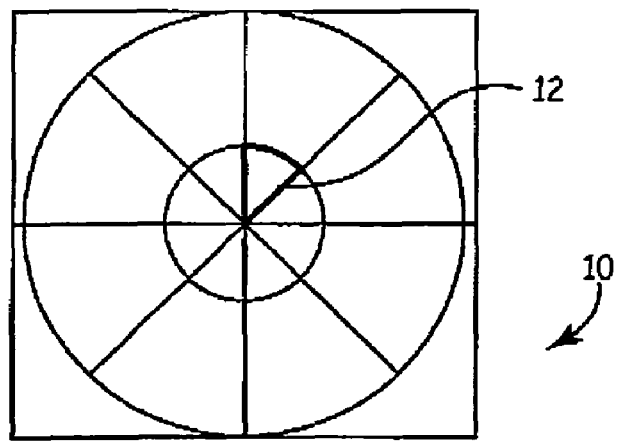
Figure 5:
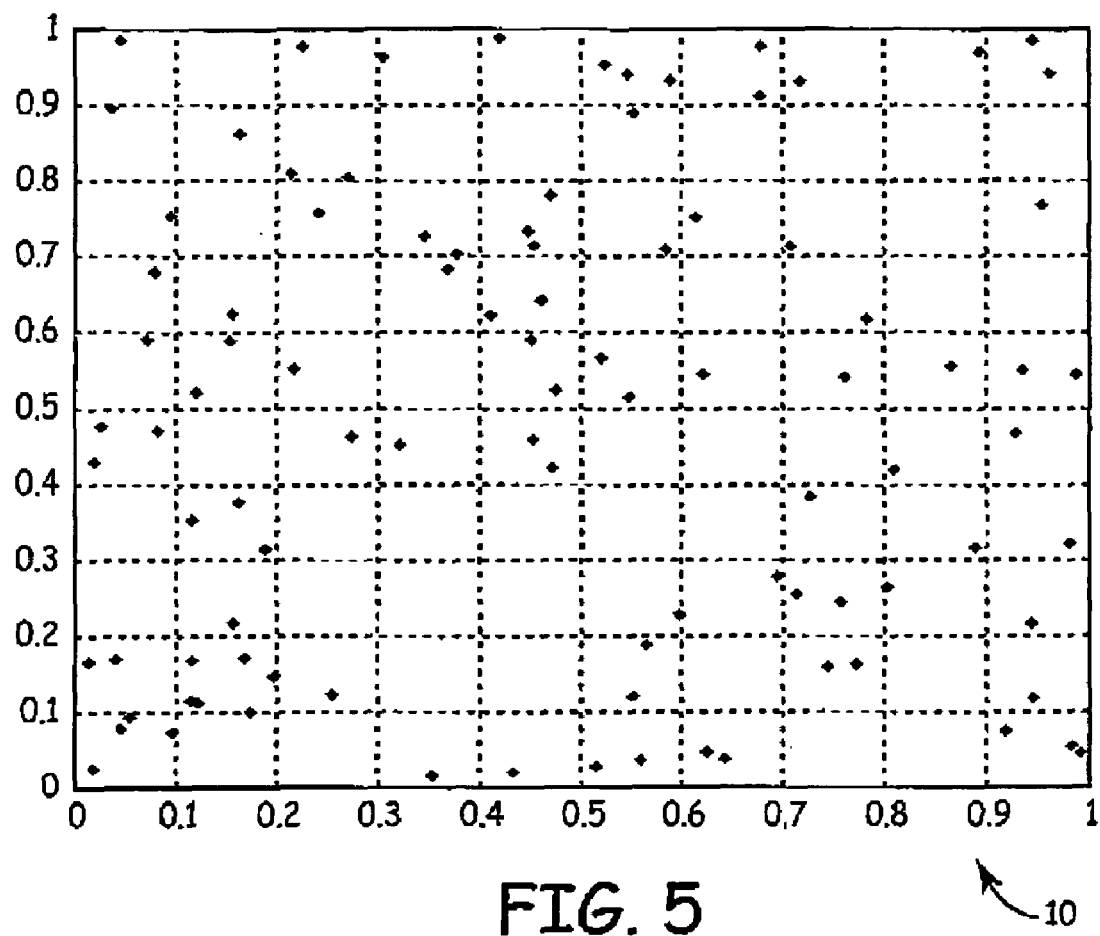
FIG. 5 is a scatter plot of a cardiac rhythm parameter, the plot having a plurality of regions formed by a linear grid pattern in accordance with an embodiment of the invention.
Figure 6:
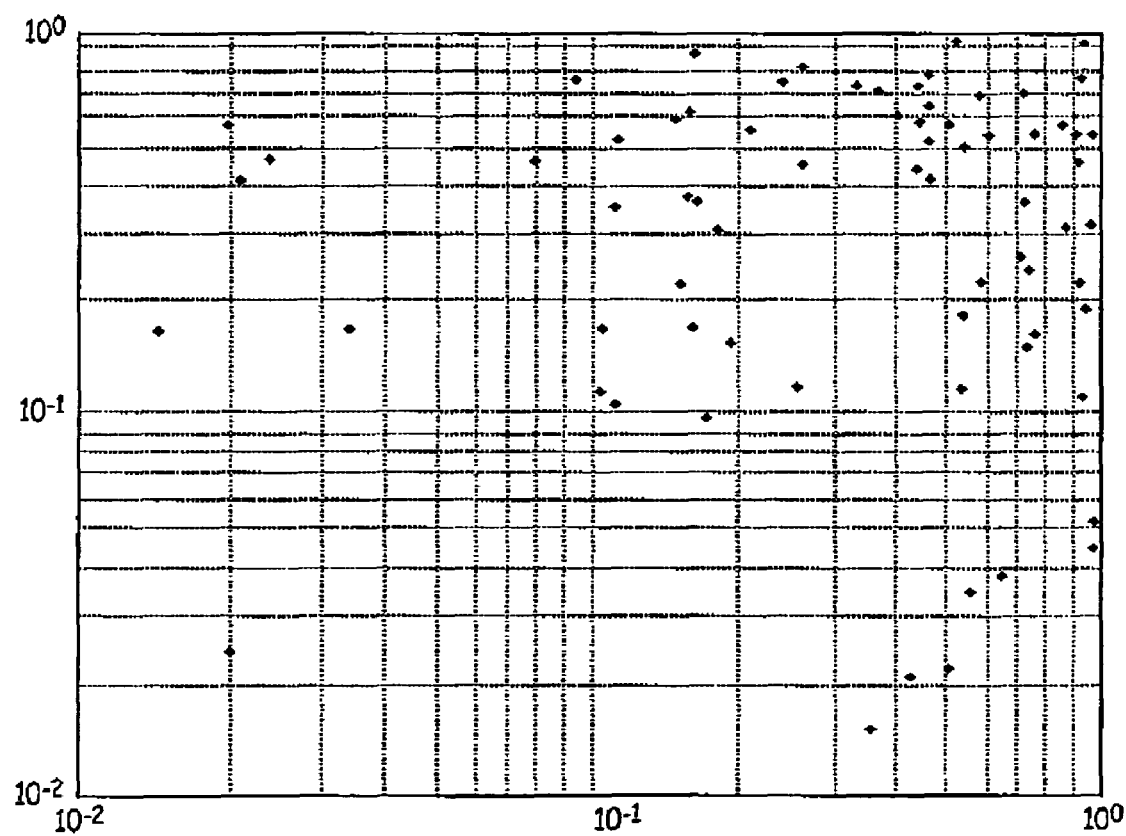
FIG. 6 is a scatter plot of the data shown in FIG. 5, the plot having a plurality of regions formed by a logarithmic grid pattern in accordance with an embodiment of the invention.

The area of the scatter plot 10 is divided into a plurality of regions 12. Each region 12 occupies a specified area of scatter plot 10, as shown in FIG. 3(b). Each point 14 is plotted into one region 12 of the scatter plot 10. This may necessitate the creation of a rule for determining which region 12 a point 14 falls within in situations where the point 14 is plotted exactly on the boundary between two regions 12. One such rule may simply be a "round up" rule, whereby a point 14 that falls exactly on a boundary between regions 12 is assigned to the "higher-valued" region, for example up and/or to the right in the scatter plot 10 shown in FIG. 3(b). FIGS. 4(a)-(c) are examples of alternate configurations of regions 12 having a shape that is not rectangular, and which occupy generally curved portions of the scatter plot 10 in accordance with various embodiments of the invention. Note that the size and shape of region 12 can also vary to suit a particular application. For example, the axes of scatter plot 10 need not be linear. FIGS. 5 and 6, for example, show the same data plotted on scatter plots having linear and logarithmic axes, respectively.

The determination of a measure of variability of a cardiac rhythm parameter is based on a graphical estimation using a region counting algorithm, as explained below. In FIG. 3(a), the irregular heart rhythm (cardiac signal 20) is plotted in scatter plot 10 of FIG. 3(b) based on a sequence of successive values of a cardiac rhythm parameter 16 derived from the cardiac signal 20. A specified number of plotted points (the "window" of plotted points) is shown plotted using the Lorentz (or Poincaré) scatter-plot technique described above. The window may, for example, be a sliding window of N points, which slides one point at a time. With a sliding window, each additional heartbeat causes a new point to be plotted, and the oldest point to be removed, so that the total number of points plotted remains equal to the window size, N. Of course, the sliding nature of the window does not have to be updated with each additional heartbeat; a window of N points could be plotted at periodic intervals, for example, with or without overlap between successive windows.

With continued reference to FIG. 3(b), scatter plot 10 is shown divided into a plurality of regions 12. The regions 12 shown in the particular embodiment of FIG. 3(b) are comprised of rectangular boxes forming a grid pattern throughout the area of scatter plot 10. As noted above, the regions 12 need not be rectangular or square in shape. The axes of scatter plot 10 shown FIG. 3(b) range from 150 $min^{-1}$ to 400 $min^{-1}$ in a linear grid plot, reflecting a range of atrial rates (which may be derived from P-P intervals, for example). It should be noted that the axes of scatter plot 10 need not be linear, nor does it need to reflect rate or interval information. EGM slope and amplitude are examples of other cardiac rhythm parameters that may also be plotted, among other possible cardiac rhythm parameters. FIGS. 5 and 6 reflect the same cardiac rhythm parameter data plotted on linear and logarithmic scatter plots, respectively.

To provide a measure of the variability of the cardiac rhythm parameter being plotted, a count is made of the number of regions 12 in which at least one point is plotted. Thus, the variability of the cardiac rhythm parameter may be represented as a number, equal to the number of regions counted containing one or more plotted points. Optionally, the variability may be expressed as a percentage, for example:

Variability=[# regions with at least 1 point/$N$ points]×100%      Eqn 1:

or

Variability=[# regions with at least 1 point/total # regions]×100%.      Eqn 2:

In one embodiment of the invention, the counting of regions containing one or more plotted points may be weighted by using a weighting factor. For example, in certain embodiments of the invention, it may be desirable to discount the effect on variability of points that fall in regions that are very close to certain specified areas of the scatter plot (areas that tend to have a high concentration of points plotted therein, for example). It may likewise be desirable to increase the effect on variability of points that fall in regions that tend to have a low concentration of plotted points. Thus, a weighting factor may be assigned to each region based upon its location within the scatter plot to thereby affect the measurement of variability.

Figure 8:
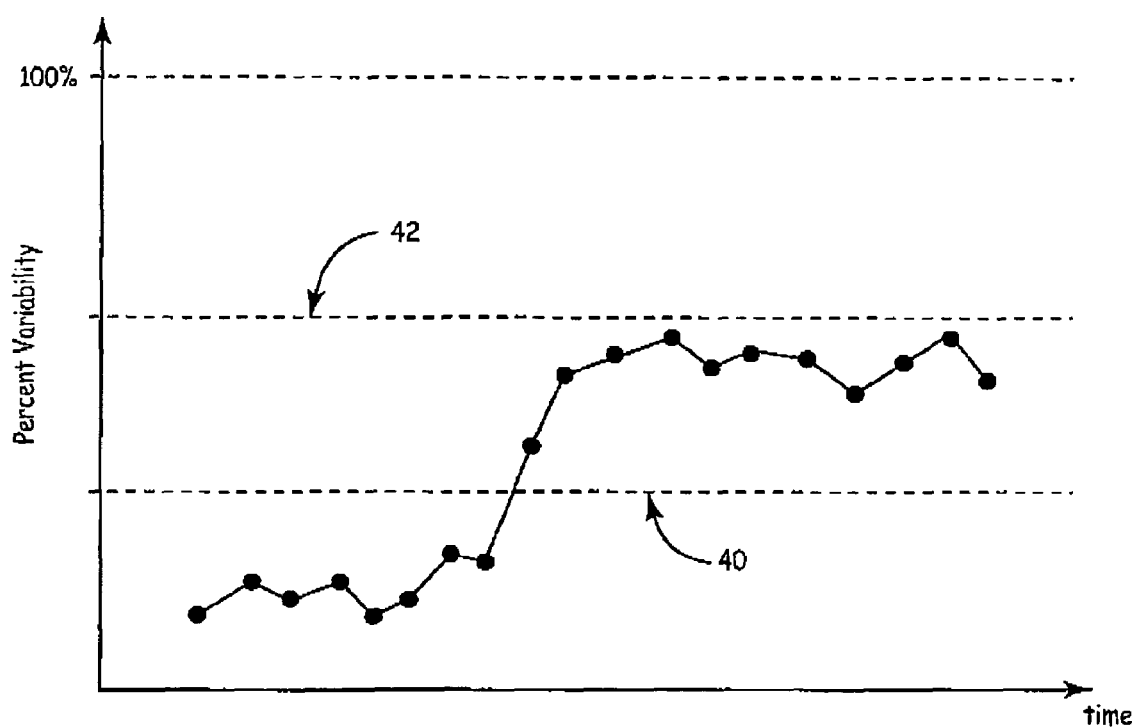
FIG. 8 is a plot of a measure of variability as a function of time in accordance with an embodiment of the invention.

FIG. 8 shows a plot of variability over time, with each point plotted corresponding to a measured value of variability (percentage variability is shown in FIG. 8). As noted above, each measured value of variability is calculated based upon a window of N points. The window may "slide" one point at a time, or may be based on windows of N points that are "staggered" from one another by a specified number of points or by a specified amount of time, for example. FIG. 8 indicates a threshold 40 (dashed line) for differentiating types of arrhythmias based upon the measure of variability. In some embodiments of the invention, additional thresholds (such as threshold 42) may also be used to further refine the arrhythmia classification. A measured variability that is above a specified threshold, for example, may be used to identify an atrial arrhythmia as AF rather than AFL. In one embodiment of the invention, rate information may be used in conjunction with a comparison of the measure of variability to a threshold. For example, an atrial rate of 350 bpm may be classified as either AF or AFL based on rate information alone. A variability that is above a specified threshold may indicate or confirm the presence of AF, while a variability that is below a specified threshold may indicate or confirm the presence of AFL according to certain embodiments of the invention.

In FIG. 3(b), 100 points are plotted in scatter plot 10 based upon a series of P-P intervals converted into atrial rate information in this example. Scatter plot 10 is divided into a plurality of regions 12. In this particular example, the regions 12 are formed by grid lines arranged on scatter plot 10 such that the spacing between grid lines corresponds to a change in atrial rate of 16 beats per minute ($min^{-1}$). Each region 12 therefore occupies a space of 16×16 $min^{-1}$. The number of regions 12 containing one or more plotted points 14 is then counted to obtain a measure of variability. In FIG. 3(b), for example, a total of 33 regions 12 have one or more points 14 plotted therein. In percentage terms, the resulting measure of variability may be stated as 33%, since the total number of plotted points 14 is 100.

Figure 7:
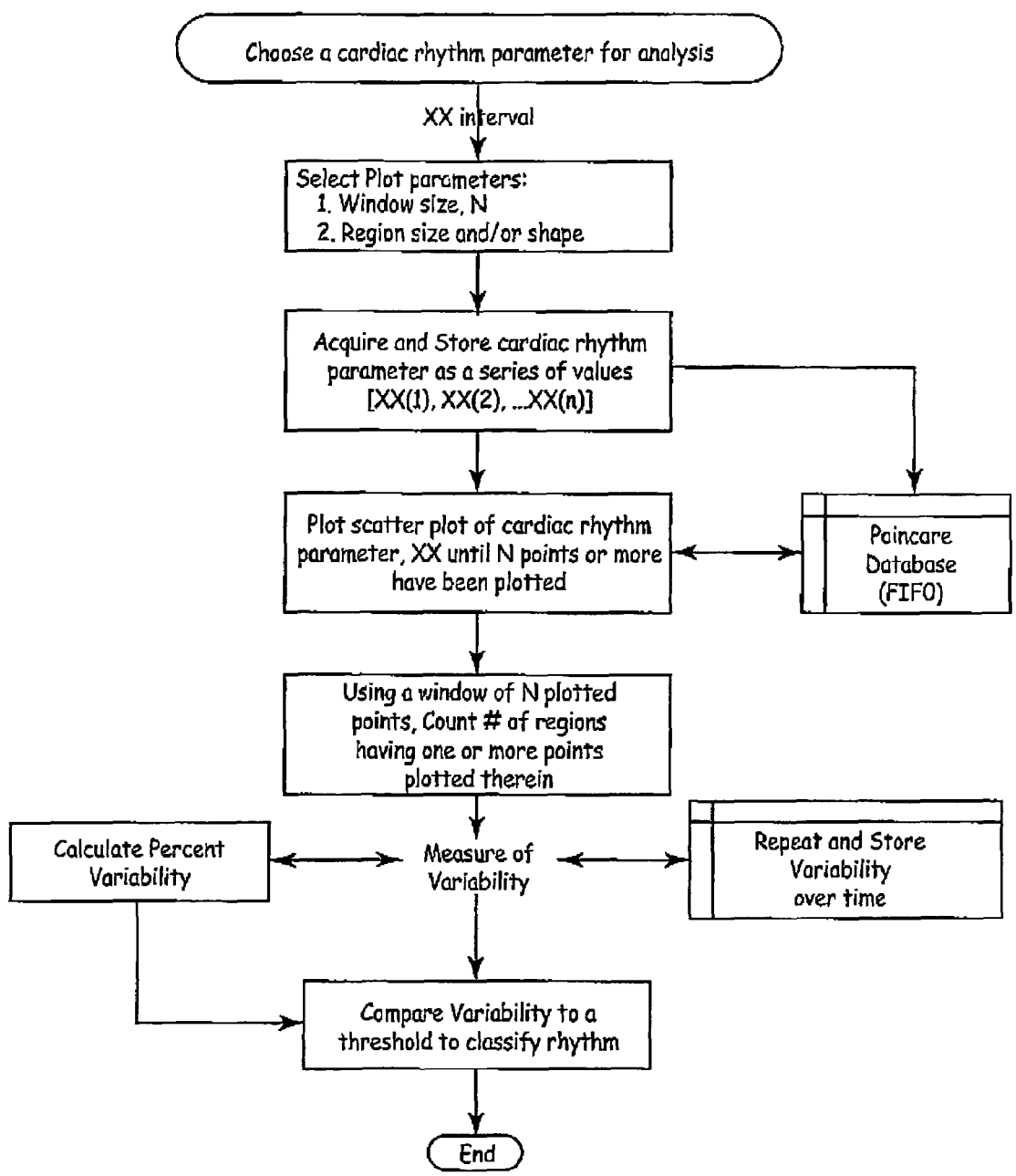
FIG. 7 is a flowchart showing the steps in a process of calculating a measure of variability from a scatter plot in accordance with an embodiment of the invention.

The process followed in calculating the measure of variability is generally summarized in FIG. 7, which defines the following steps:
 1. Choose a cardiac rhythm parameter (e.g., P-P interval).
 2. Select region size/shape and window size, N.
 3. Acquire and store cardiac rhythm parameter in a database.
 4. Plot cardiac rhythm parameter in a scatter plot until N points are plotted.
 5. Calculate measure of variability by counting the number of regions containing one or more plotted points.
 6. (Optional) Calculate percent variability.
 7. Compare variability to a threshold to classify the rhythm.
 8. (Optional) Repeat variability calculation over time.

The variability of the cardiac rhythm parameter is determined by "drawing" a Lorentz plot of a number of preceding heart beats (window size) onto a scatter plot having a certain region or grid size and shape (resolution). Varying the window size and/or region size/shape may have an influence on the calculated variability.

In FIG. 3(b), a total of one hundred points 14 were plotted, corresponding to a window size (or width) of 100 (N=100). The choice of N may reflect a trade-off between the desire for calculational simplicity (or speed), and the desire for accuracy or stability. For example, a smaller window N may provide a result sooner (i.e., not as many beats are required, and less memory storage may be needed). A smaller window N may also reflect changes in the measured variability sooner, since the window will not be as heavily weighted with "old" plotted points 14. A smaller window N may also tend to reflect information that is more local or transient in nature. A larger window N, by contrast, while possibly requiring larger memory storage and computational resources, may tend to produce a measured variability that is more "stable," since it is "averaging" a larger quantity of data into a numerical result. A larger window may also tend to reflect information that is more global in nature.

The "grid" (or region) resolution in the example of FIG. 3(b) was based upon a linear, square-shaped region having 16×16 $min^{-1}$ dimensions. The resolution may be affected by the choice of size and shape of the regions used. For example, a choice of larger regions may result in a smaller number of regions containing one or more plotted points, thereby resulting in a lower measure of variability, according to Eqn. 1. (Note: The variability measured by Eqn. 2 may be smaller, larger, or may be unaffected by changing the size of the regions.) Conversely, selecting smaller regions may result in more regions being counted, thereby producing a higher measure of variability, according to Eqn. 1.

The selections of window size N and region size and/or shape may be affected by a variety of factors, such as the particular cardiac rhythm parameter being analyzed, patient history, known sensing issues (FFRWs, undersensing), etc. The selections regarding window size and region size/shape may also be affected by the rate/interval of the particular cardiac rhythm parameter or of the overall heart rate of the patient. In one embodiment of the invention, a calculation of rate/interval is made in conjunction with the variability measurement. The rate/interval may be an average rate based upon a certain number of beats, R; the number of beats R used to calculate rate may also be a parameter that can be selected and varied in accordance with certain embodiments of the invention.

It should be noted that physically "drawing" or "plotting" the scatter plot 10 is not a required step. For example, the process of plotting points in a scatter plot may be performed by a memory device and logic circuitry and/or software instructions that are capable of identifying and recording which region 12 a point would fall into, and incrementing (and decrementing) counters to keep track of the points 14 that fall within each of the regions 12. (Decrementing of a counter would occur, for example, when the sliding window of N points causes the oldest point 14 to be removed from the window, and hence, from the affected region 12.) Each region 12 may, in such an embodiment, comprise a data bin for storing the number of points 14 that fall within a region, based on logic circuitry and counters, for example. Additional logic circuitry and/or a counter may determine the measure of variability by counting the total number of data bins that has one or more points stored therein.

The methods of classifying arrhythmias disclosed herein are relatively simple to implement, and may be performed by an Implantable Medical Device (IMD). For example, the steps of plotting points and counting regions can be accomplished with logic circuitry such as comparators, counters, and memory. Calculating percent variability may require additional components and/or instructions capable of performing division, for example. Comparing the measured variability to a threshold may also require a comparator. All of these functions may be incorporated in the circuitry of an IMD, and may further be performed in real-time, e.g., to select and/or deliver an appropriate therapy based upon the arrhythmia classification. The advantages in computational simplicity described above typically result in a reduced need for memory and processing power, which may result in reduced battery capacity requirements, reduced memory storage requirements, smaller device sizes, faster responses, etc.

The region-counting approach to measuring variability of a cardiac rhythm parameter may also be less sensitive to certain sensing problems like far-field R-waves (FFRWs) and undersensing. Due to the typically repetitive (regular) nature of FFRWs and 2:1 blanking, for example, these beats typically end up plotted into a fairly small number of regions in the Lorentz plot and therefore may not significantly affect the measured variability. Additionally, certain sensing problems (such as severe undersensing) may not be reflected, for example, if the Lorentz plot only plots events above (or below) a certain amount (e.g., only atrial rates greater than 100 min−1). In other words, even if certain sensing problems exist, they may not have a significant effect on the measurement of variability.

Thus, embodiments of a METHOD OF AND APPARATUS FOR CLASSIFYING ARRHYTHMIAS USING SCATTER PLOT ANALYSIS are disclosed. One skilled in the art will appreciate that the invention can be practiced with embodiments other than those disclosed. The disclosed embodiments are presented for purposes of illustration and not limitation, and the invention is limited only by the claims that follow.

What is claimed is:

1. A computer-readable medium programmed with instructions for performing a method of classifying arrhythmias, the medium comprising instructions for causing a programmable processor to:
   acquire a cardiac signal;
   derive a recurring cardiac rhythm parameter from the cardiac signal and store the parameter as a series of values;
   plot a point on a scatter plot for each pair of successive stored values,
      wherein
      an abscissa of the point is a first value of a pair of successive stored values, and
      an ordinate of the point is a second value of the pair of successive stored values,
      and wherein the scatter plot is divided into a plurality of regions;
   derive a measure of variability by counting sum up the number of regions that have one or more points plotted therein; and
   compare the measure of variability to a threshold.

2. The medium of claim 1, the instructions further causing the processor to continue plotting a point on a scatter plot until at least a specified number, N, of points have been plotted such that a window of N plotted points is available for the step of deriving a measure of variability.

3. The medium of claim 1 wherein the plurality of regions includes generally rectangular portions of the scatter plot.

4. The medium of claim 1 wherein the plurality of regions includes generally curved portions of the scatter plot.

5. The medium of claim 1 wherein the recurring cardiac rhythm parameter is derived from R-R intervals of the cardiac signal.

6. The medium of claim 1 wherein the recurring cardiac rhythm parameter is derived from P-P intervals of the cardiac signal.

7. The medium of claim 1 wherein the recurring cardiac rhythm parameter is derived from an amplitude of a portion of the cardiac signal.

8. The medium of claim 7 wherein the recurring cardiac rhythm parameter is a slope of a portion of the cardiac signal.

9. The medium of claim 1, the instructions further causing the processor to select a therapy based on the result of comparing the measure of variability to a threshold.

10. The medium of claim 1, the instructions further causing the processor to measure a rate derived from a recurring cardiac rhythm parameter.

11. The medium of claim 10, the instructions further causing the processor to compare the rate to a threshold.

12. The medium of claim 11, the instructions further causing the processor to classify an arrhythmia based on the steps of comparing the measure of variability to a threshold and comparing the rate to a threshold.

13. The medium of claim 12 wherein the arrhythmia is classified as atrial fibrillation (AF) when the rate and variability meet specified AF criteria.

14. The medium of claim 12 wherein the arrhythmia is classified as atrial flutter (AFL) when the rate and variability meet specified AFL criteria.

15. The medium of claim 1, the instructions further causing the processor to divide the number of regions counted containing one or more plotted points by the number of points in the window, N, to calculate a percent variability.

16. The medium of claim 1, the instructions further causing the processor to weight the value of each plotted point by a weighting factor during the step of counting the number of regions that contain one or more plotted points, the weighting factor capable of varying by region in the scatter plot.

17. A system for classifying arrhythmias, the system comprising:

a sensor for acquiring a cardiac signal;

first processing means for deriving a recurring cardiac rhythm parameter from the cardiac signal and storing the parameter as a series of values;

a database for plotting a point on a scatter plot for each pair of successive stored values, wherein an abscissa of the point is a first value of a pair of successive stored values, and an ordinate of the point is a second value of the pair of successive stored values, and wherein the scatter plot is divided into a plurality of regions;

second processing means for deriving a measure of variability by counting the number of regions that have one or more points plotted therein; and a comparator for comparing the measure of variability to a threshold.

* * * * *

UNITED STATES PATENT AND TRADEMARK OFFICE
CERTIFICATE OF CORRECTION

PATENT NO. : 7,657,307 B2   Page 1 of 1
APPLICATION NO. : 11/263184
DATED : February 2, 2010
INVENTOR(S) : Van Dam et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Thirtieth Day of November, 2010

David J. Kappos
*Director of the United States Patent and Trademark Office*